United States Patent [19]
> Aoyama et al.

[11] Patent Number: 5,326,913
[45] Date of Patent: Jul. 5, 1994

[54] PROCESS FOR PREPARING FLUORINATED COMPOUND

[75] Inventors: Hirokazu Aoyama; Satoshi Koyama, both of Osaka, Japan

[73] Assignee: Daikin Industries Ltd., Osaka, Japan

[21] Appl. No.: 897,261

[22] Filed: Jun. 11, 1992

[30] Foreign Application Priority Data

Jun. 14, 1991 [JP] Japan .................. 3-143088

[51] Int. Cl.5 ............................................. C07C 17/26
[52] U.S. Cl. ............................................. 570/172
[58] Field of Search ................................ 570/172

[56] References Cited

U.S. PATENT DOCUMENTS

| 3,308,175 | 3/1967 | Barr ............. | 570/172 |
| 3,795,710 | 3/1974 | Seigneurin ....... | 570/172 |
| 4,740,640 | 4/1988 | Boutevin et al. . | |
| 5,157,171 | 10/1992 | Sievent et al. .. | 570/172 |
| 5,177,274 | 1/1993 | Aoyama et al. ... | 570/172 |

FOREIGN PATENT DOCUMENTS

| 0183590 | 6/1986 | European Pat. Off. . |
| 0421322 | 4/1991 | European Pat. Off. . |
| 0436903 | 7/1991 | European Pat. Off. . |

*Primary Examiner*—Alan Siegel
*Attorney, Agent, or Firm*—Birch, Stewart, Kolasch & Birch

[57] ABSTRACT

A fluorinated compound of the formula:

$$R-CCl_2CF_2CF_3 \qquad (I)$$

in which R is a perfluoroalkyl group, a perchloroalkyl group, a polyfluoroalkyl group, a polychloroalkyl group or a polychloropolyfluoroalkyl group, each having at least one carbon atom is prepared at a high selectivity and a high yield by reacting tetrafluoroethylene with a compound of the formula:

$$R-CFCl_2 \qquad (II)$$

in which R is the same as defined above in the presence of a Lewis acid.

17 Claims, No Drawings

PROCESS FOR PREPARING FLUORINATED COMPOUND

BACKGROUND OF THE INVENTION

1. Field of the Invention

The present invention relates to a process for preparing a fluorinated compound, in particular, a fluorinated compound of the formula:

$$R\text{---}CCl_2CF_2CF_3 \qquad (I)$$

wherein R is a perfluoroalkyl group, a perchloroalkyl group, a polyfluoroalkyl group, a polychloroalkyl group or a polychloropolyfluoroalkyl group, each having at least one carbon atom.

The fluorinated compound (I) to be prepared by the process of the present invention is useful as an intermediate for the preparation of a hydrochlorofluorocarbon and hydrofluorocarbon which limits destruction of the ozone layer or other fluorinated compounds.

2. Description of the Related Art

It is known that a fluorinated compound having three carbon atoms is produced, when a halomethane having one carbon atom (e.g. tetrachloromethane, trichlorofluoromethane and dichlorofluoromethane) and a fluorine-containing ethylene (e.g. tetrafluoroethylene, trifluoroethylene, chlorotrifluoroethylene and 1,1-dichloro-2,2-difluoroethylene) are addition reacted in the presence of anhydrous aluminum chloride. However, no addition reaction of a haloalkane having at least two carbon atoms with the fluorine-containing ethylene such as tetrafluoroethylene in the presence of a Lewis acid such as anhydrous aluminum chloride has been known.

SUMMARY OF THE PRESENT INVENTION

An object of the present invention is to provide a process for preparing the above fluorinated compound (I) at a high selectivity and a high yield.

According to the present invention, there is provided a process for preparing a fluorinated compound of the formula:

$$R\text{---}CCl_2CF_2CF_3 \qquad (I)$$

wherein R is a perfluoroalkyl group, a perchloroalkyl group, a polyfluoroalkyl group, a polychloroalkyl group or a polychloropolyfluoroalkyl group, each having at least one carbon atom, which process comprises reacting tetrafluoroethylene with a compound of the formula:

$$R\text{---}CFCl_2 \qquad (II)$$

wherein R is the same as defined above in the presence of a Lewis acid.

DETAILED DESCRIPTION OF THE INVENTION

In the formulas (I) and (II), the group R has at least one carbon atom, preferably 1 to 10 carbon atoms, more preferably 1 to 4 carbon atoms.

Specific examples of the compound (I) are $CF_3CFCl_2$, $CF_3CF_2CFCl_2$, $ClCF_2CFCl_2$, $ClCF_2CFClCFCl_2$, $CFCl_2CF_2\text{-}CFCl_2$, $CF_3CF_2CF_2CFCl_2$, $ClCF_2CFClCF_2CFCl_2$, $HCF_2CF_2CFCl_2$, $HCF_2CF_2CF_2CF_2CFCl_2$ and the like.

The catalyst to be used in the present reaction is a Lewis acid. Examples of the Lewis acid are chlorides such as anhydrous aluminum chloride, anhydrous zirconium tetrachloride, anhydrous zinc chloride, anhydrous tin chloride, anhydrous titanium tetrachloride, anhydrous iron chloride, anhydrous antimony pentachloride, etc., chlorofluorides such as these chlorides a part of chlorine atoms is replaced with fluorine atoms, and the like. Among them, anhydrous aluminum chloride, anhydrous zirconium tetrachloride, anhydrous aluminum chlorofluoride and anhydrous zirconium chlorofluoride are preferred.

As the Lewis acid, any commercially available one in a particle, powder or liquid form may be used.

Alternatively, aluminum chlorofluoride of the formula:

$$AlCl_xF_y \qquad (III)$$

wherein x is a number larger than 0 and smaller than 3, and y is a number larger than 0 and smaller than 3, provided that a sum of x and y is 3, or zirconium chlorofluoride of the formula:

$$ZrCl_pF_q \qquad (IV)$$

wherein p is a number larger than 0 and smaller than 4, and q is a number larger than 0 and smaller than 4, provided that a sum of p and q is 4 is prepared by treating anhydrous aluminum chloride or zirconium tetrachloride with hydrogen fluoride, hydrofluoric acid or a chlorofluorocarbon, fluorohydrocarbon or chlorofluorohydrocarbon having 1 to 4 carbon atoms, preferably 1 or 2 carbon atoms (e.g. trifluoromethane, tetrafluoroethane, chlorodifluoromethane, dichlorofluoromethane, trifluorodichloroethane, trifluorochloromethane, dichlorodifluoromethane, trichlorofluoromethane, difluorotetrachloroethane, trifluorotrichloroethane, etc.).

In the above preparation step, hydrogen fluoride, hydrofluoric acid, the chlorofluorocarbon, fluorohydrocarbon or chlorofluorohydrocarbon may be reacted alone, or a mixture of two or more of them may be reacted.

The reaction temperature is from 0° to 120° C., preferably from 0° to 100° C. The above fluorination compound may be contacted with anhydrous aluminum chloride or zirconium tetrachloride in the liquid state or the gas state.

An amount of the Lewis acid is a catalytic amount and usually from 0.1 to 20% by weight, preferably from 0.25 to 10% by weight based on the weight of the starting compound (II).

Tetrafluoroethylene is added till the reaction finishes. An amount of tetrafluoroethylene is usually from 1 to 1.5 equivalents with respect to the compound (II). Though a larger amount of tetrafluoroethylene may be added, an excess amount of tetrafluoroethylene does not participate in the reaction and a recycling amount increases. Tetrafluoroethylene may be used in a gas state or a liquid state.

A reaction temperature in the process of the present invention is usually from −20° C. to +150° C., preferably from −20° C. to +100° C. When the reaction temperature is lower than −20° C., a reaction rate is too low and unpractical. When the reaction temperature is higher than 150° C., side reactions may take place and undesirable by-products are formed.

A reaction pressure depends on the reaction temperature and is usually from atmospheric pressure to 20 kg/cm²G, preferably from atmospheric pressure to 15 kg/cm²G.

The reaction of the present invention may be carried out in the presence of a solvent. Preferred examples of the solvent are carbon tetrachloride, chloroform, methylene chloride, 1,1,1-trichloro-2,2,2-trifluoroethane, 1,2-dichlorotetrafluoroethane, 3,3-dichloro-1,1,1,2,2-pentafluoropropane, 1,3-dichloro-1,1,2,2,3-pentafluoropropane and the like. In addition, the produced compound (I) may be used as a solvent. In this case, no separation of the reaction product from the solvent is necessary and this mode is economically advantageous.

PREFERRED EMBODIMENTS OF THE INVENTION

The present invention will be illustrated by following Examples.

Example 1

In a stainless steel 200 ml autoclave equipped with a stirrer, anhydrous aluminum chloride (2 g) was charged. After reducing the pressure in the autoclave and cooling to $-20°$ C., 1,1-dichlorotetrafluoroethane (65 g) was charged. After heating up to 80° C. gaseous tetrafluoroethylene was injected till the pressure reached 13 kg/cm²G. As the reaction proceeded, tetrafluoroethylene was consumed and the pressure dropped. While maintaining the temperature at 80° C., tetrafluoroethylene was added to maintain the pressure at 13 kg/cm²G. After 15 hours, no pressure drop was observed. The autoclave was cooled to 0° C., and unreacted tetrafluoroethylene was purged.

A content in the autoclave was analyzed by gas chromatography to find that desired 2,2-dichlorooctafluorobutan ($CF_3CCl_2CF_2CF_3$) was produced at a yield of 75% (based on the amount of 1,1-dichlorotetrafluoroethane).

Example 2

In the same autoclave as used in Example 1, anhydrous aluminum chloride (2 g) and trichlorofluoromethane (11 g) were charged. After stirring at room temperature for 3 hours, unreacted trichlorofluoromethane, and carbon tetrachloride, dichlorodifluoromethane and trifluorochloromethane which were formed from trichlorofluoromethane were removed under reduced pressure. Thereby, aluminum chlorofluoride was prepared.

After reducing the pressure in the autoclave and cooling to $-20°$ C., 1,1-dichlorotetrafluoroethane (65 g) was charged. After heating up to 20° C., gaseous tetrafluoroethylene was injected till the pressure reached 5 kg/cm²G. Immediately the reaction started and heat was generated. While cooling the autoclave with iced water to maintain the reaction temperature at 20° C. or lower, tetrafluoroethylene was added to 5 kg/cm²G. After 4 hours, tetrafluoroethylene was not absorbed and the reaction was stopped. The autoclave was cooled to 0° C., and unreacted tetrafluoroethylene was purged.

A content in the autoclave was analyzed by gas chromatography to find that desired 2,2-dichlorooctafluorobutane ($CF_3CCl_2CF_2CF_3$) was produced at a yield of 83% (based on the amount of 1,1-dichlorotetrafluoroethane).

Example 3

In the same manner as in Example 2, the same amount of aluminum chlorofluoride was prepared in the autoclave. After charging 1,1,3,4-tetrachlorohexafluorobutane (78.5 g), the pressure in the autoclave was reduced, and then gaseous tetrafluoroethylene was injected at 70° C. till the pressure reached 7 kg/cm²G. As the reaction proceeded, tetrafluoroethylene was consumed and the pressure dropped. While maintaining the temperature at 70° C., tetrafluoroethylene was added to maintain the pressure at 7 kg/cm²G. After 13 hours, unreacted tetrafluoroethylene was purged.

A content in the autoclave was analyzed by gas chromatography to find that desired 3,3,5,6-tetrachlorodecafluorohexane was produced at a yield of 85% (based on the amount of tetrachlorohexafluorobutane).

Example 4

In the same manner as in Example 2 but using 1,1-dichlorohexafluoropropane (70 g) in place of 1,1-dichlorotetrafluoroethane, the reaction was carried out to obtain desired 3,3-dichlorodecafluoropentane ($CF_3CF_2CCl_2CF_2CF_3$) at a yield of 92% (based on the amount of dichlorohexafluoropropane).

Example 5

In a 200 ml glass flask equipped with a silica gel drying tube to prevent water from flowing into the flask and a gas inlet tube, 2,2-dichlorooctafluorobutane (40 g) and aluminum chlorofluoride (2 g) which was prepared in the same manner as in Example 2 were charged. While stirring the mixture with a magnetic stirrer, tetrafluoroethylene and 1,1-dichlorotetrafluoroethane were supplied through the gas inlet tube at flow rates of 20 ml/min. and 18 ml/min., respectively after premixing them. During this period, the flask was cooled with iced water from exterior to adjust the reaction temperature at 5° to 10° C. As the reaction time passed, an amount of 2,2-dichlorooctafluorobutane increased. After 5 hours, an amount of the reaction mixture increased to 99 g. The reaction mixture was analyzed by gas chromatography to find that the mixture contained 96% of 2,2-dichlorooctafluorobutane. This means that 55 g of 2,2-dichlorooctafluorobutane was produced.

Example 6

In the same manner as in Example 2 but using anhydrous zirconium tetrachloride (2 g) in place of anhydrous aluminum chloride, the reaction was carried out. Desired 2,2-dichlorooctafluorobutane ($CF_3CCl_2CF_2CF_3$) was obtained at a yield of 92% (based on the amount of 2,2-dichlorotetrafluoroethane).

What is claimed is:

1. A process for preparing a fluorinated compound of the formula:

$$R-CCl_2CF_2CF_3 \qquad (I)$$

wherein R is a perfluoroalkyl group, a perchloroalkyl group, a polyfluoroalkyl group, a polychloroalkyl group or a polychloropolyfluoroalkyl group, each having at least one carbon atom, which process comprises reacting, at a reaction temperature from $-20°$ C. to $+150°$ C., tetrafluoroethylene with a compound of the formula:

R—CFCl$_2$      (II)

wherein R is the same as defined above, in the presence of a Lewis acid, wherein said Lewis acid is at least one member selected from the group consisting of anhydrous aluminum chloride, anhydrous zirconium tetrachloride, anhydrous zinc chloride, anhydrous tin chloride, anhydrous titanium tetrachloride, anhydrous iron chloride, anhydrous antimony pentachloride, anhydrous aluminum chlorofluoride, anhydrous zirconium chlorofluoride, anhydrous zinc chlorofluoride, anhydrous tin chlorofluoride, anhydrous titanium chlorofluoride, anhydrous iron chlorofluoride and anhydrous antimony chlorofluoride.

2. The process according to claim 1, wherein said compound (II) is at least one compound selected from the group consisting of CF$_3$CFCl$_2$, CF$_3$CF$_2$CFCl$_2$, ClCF$_2$CFCl$_2$, ClCF$_2$CFClCFCl$_2$, CFCl$_2$CF$_2$CFCl$_2$, CF$_3$CF$_2$CF$_2$CFCl$_2$, ClCF$_2$CFClCF$_2$CFCl$_2$, HCF$_2$CF$_2$CFCl$_2$ and HCF$_2$CF$_2$CF$_2$CF$_2$CFCl$_2$.

3. The process according to claim 1, wherein said Lewis acid is at least one chloride selected from the group consisting of anhydrous aluminum chloride, anhydrous zirconium tetrachloride, anhydrous zinc chloride, anhydrous tin chloride, anhydrous titanium tetrachloride, anhydrous iron chloride and anhydrous antimony pentachloride.

4. The process according to claim 1, wherein said Lewis acid is at least one chlorofluoride selected from the group consisting of anhydrous aluminum chlorofluoride, anhydrous zirconium chlorofluoride, anhydrous zinc chlorofluoride, anhydrous tin chlorofluoride, anhydrous titanium chlorofluoride, anhydrous iron chlorofluoride and anhydrous antimony chlorofluoride.

5. The process according to claim 1, wherein said Lewis acid is anhydrous aluminum chlorofluoride of the formula:

AlCl$_x$F$_y$      (III)

wherein x is a number larger than 0 and smaller than 3, and y is a number larger than 0, and smaller than 3, provided that a sum of x and y is 3.

6. The process according to claim 1, wherein said Lewis acid is anhydrous zirconium chlorofluoride of the formula:

ZrCl$_p$F$_q$      (IV)

wherein p is a number larger than 0 and smaller than 4, and q is a number larger than 0 and smaller than 4, provided that a sum of p and q is 4.

7. The process according to claim 1, wherein an amount of said Lewis acid is from 0.1 to 20% by weight based on the weight of said compound (II).

8. The process according to claim 1, wherein an amount of said Lewis acid is from 0.1 to 20% by weight based on the weight of said compound (II).

9. The process according to claim 1, wherein the tetrafluoroethylene is present in an amount of from 1 to 1.5 equivalents with respect to compound (II).

10. The process according to claim 1, wherein the reaction temperature is from −20° C. to +100° C.

11. The process according to claim 1, wherein the process is conducted at from atmospheric pressure to 15 kg/cm$^2$G.

12. The process according to claim 1, wherein the process is conducted in the presence of a solvent selected from the group consisting of carbon tetrachloride, chloroform, methylene chloride, 1,1,1-trichloro-2,2,2-trifluoroethane, 1,2-dichlorotretrafluoroethane, 3,3-dichloro-1,1,1,2,2-pentafluoropropane and 1,3-dichloro-1,1,2,2,3-pentafluoropropane.

13. The process according to claim 1, wherein said Lewis acid is selected from the group consisting of anhydrous aluminum chloride, anhydrous zirconium tetrachloride, anhydrous aluminum chlorofluoride, and anhydrous zirconium chlorofluoride.

14. A process for preparing a fluorinated compound of the formula:

R—CCl$_2$CF$_2$CF$_3$      (I)

wherein R is a perfluoroalkyl group, a perchloroalkyl group, a polyfluoroalkyl group, a polychloroalkyl group or a polychloropolyfluoroalkyl group, each having at least one carbon atom, which process comprises reacting, at a reaction temperature from −20° C. to +150° C., tetrafluoroethylene with at least one compound (II) selected from the group consisting of CF$_3$CFCl$_2$, CF$_3$CF$_2$CFCl$_2$, ClCF$_2$CFCl$_2$, ClCF$_2$CFClCFCl$_2$, CFCl$_2$CF$_2$CFCl$_2$, CF$_3$CF$_2$CF$_2$CFCl$_2$, ClCF$_2$CFClCF$_2$-CFCl$_2$, HCF$_2$CF$_2$CFCl$_2$ and HCF$_2$CF$_2$CF$_2$CF$_2$CFCl$_2$ in the presence of a Lewis acid, wherein said Lewis acid is at least one member selected from the group consisting of anhydrous aluminum chloride, anhydrous zirconium tetrachloride, anhydrous zinc chloride, anhydrous tin chloride, anhydrous titanium tetrachloride, anhydrous iron chloride, anhydrous antimony pentachloride, anhydrous aluminum chlorofluoride, anhydrous zirconium chlorofluoride, anhydrous zinc chlorofluoride, anhydrous tin chlorofluoride, anhydrous titanium chlorofluoride, anhydrous iron chlorofluoride and anhydrous antimony chlorofluoride.

15. The process according to claim 14, wherein an amount of said Lewis acid is from 0.1 to 20% by weight based on the weight of said compound (II).

16. The process according to claim 15, wherein the tetrafluoroethylene is present in an amount of from 1 to 1.5 equivalents with respect to compound (II).

17. The process according to claim 16, wherein said Lewis acid is selected from the group consisting of anhydrous aluminum chloride, anhydrous zirconium tetrachloride, anhydrous aluminum chlorofluoride, and anhydrous zirconium chlorofluoride.

* * * * *